(12) United States Patent
Noda

(10) Patent No.: US 9,265,502 B2
(45) Date of Patent: Feb. 23, 2016

(54) DELIVERY ASSEMBLY FOR RESILIENT TISSUE CLAMP

(71) Applicant: INSIGHTRA MEDICAL, INC., Irvine, CA (US)

(72) Inventor: Wayne A. Noda, Mission Viejo, CA (US)

(73) Assignee: Insightra Medical, Inc., Irvine, CA (US)

( * ) Notice: Subject to any disclaimer, the term of this patent is extended or adjusted under 35 U.S.C. 154(b) by 375 days.

(21) Appl. No.: 13/898,896

(22) Filed: May 21, 2013

(65) Prior Publication Data

US 2013/0325039 A1 Dec. 5, 2013

Related U.S. Application Data

(63) Continuation-in-part of application No. 13/477,649, filed on May 22, 2012, now Pat. No. 9,125,656, and a continuation-in-part of application No. 13/240,018, filed on Sep. 22, 2011, which is a continuation of (Continued)

(51) Int. Cl.
*A61B 17/04* (2006.01)
*A61B 17/10* (2006.01)
*A61B 17/12* (2006.01)

(Continued)

(52) U.S. Cl.
CPC ............. *A61B 17/10* (2013.01); *A61B 1/00087* (2013.01); *A61B 1/00101* (2013.01); *A61B 17/12013* (2013.01); *A61B 2017/00278* (2013.01); *A61B 2017/00296* (2013.01); *A61B 2017/00893* (2013.01);

(Continued)

(58) Field of Classification Search
USPC .............. 606/140, 141, 206; 128/831; 29/235
See application file for complete search history.

(56) References Cited

U.S. PATENT DOCUMENTS 4,517,090 A   5/1985   Kersten et al.
4,548,201 A   10/1985  Yoon
(Continued)

FOREIGN PATENT DOCUMENTS

WO   9625886 A9   10/1996
WO   9629965 A1   10/1996

OTHER PUBLICATIONS

Wayne A. Noda, "Devices and Methods for Securing Tissue", file history of related U.S. Appl. No. 13/477,649, filed May 22, 2012.
(Continued)

*Primary Examiner* — Vy Bui
(74) *Attorney, Agent, or Firm* — John L. Rogitz

(57) ABSTRACT

A delivery assembly includes a ring sleeve that fits snugly over a main endoscope on the distal end of the endoscope. An extension tube projects distally away from the ring sleeve and may be made integrally with the sleeve. The extension tube is off-axis from the ring sleeve and endoscope. A tube-like inner carrier is reciprocatingly disposed inside the extension tube. One or more resilient tissue compression rings are placed in a stretched configuration on the inner carrier. To push the rings off the carrier, the carrier is pulled proximally within the extension tube and the compression ring is thus pulled into contact with the distal end of the extension tube. Continued pulling of the carrier causes the compression ring to be pushed off the assembly onto target tissue, at which point the ring is relaxed to assume a small configuration and clamp the target tissue.

20 Claims, 2 Drawing Sheets

Related U.S. Application Data application No. 12/141,391, filed on Jun. 18, 2008, now Pat. No. 8,062,308.

(60) Provisional application No. 61/492,289, filed on Jun. 1, 2011, provisional application No. 60/982,083, filed on Oct. 23, 2007, provisional application No. 61/012,124, filed on Dec. 7, 2007.

(51) Int. Cl.
*A61B 1/00* (2006.01)
*A61B 17/00* (2006.01)
*A61B 17/064* (2006.01)
*A61B 17/30* (2006.01)

(52) U.S. Cl.
CPC ............. *A61B 2017/0641* (2013.01); *A61B 2017/12018* (2013.01); *A61B 2017/306* (2013.01)

(56) References Cited

U.S. PATENT DOCUMENTS

| | | | |
|---|---|---|---|
| 4,820,304 A | 4/1989 | Depel et al. | |
| 5,976,158 A | 11/1999 | Adams et al. | |
| 5,980,537 A * | 11/1999 | Ouchi | A61B 17/12013 606/140 |
| 6,849,078 B2 | 2/2005 | Durgin et al. | |
| 7,189,247 B1 * | 3/2007 | Zirps | A61B 1/00087 606/140 |
| 7,641,652 B2 * | 1/2010 | Coe et al. | 606/49 |
| 7,766,020 B2 | 8/2010 | Chininis et al. | |
| 7,819,895 B2 | 10/2010 | Ginn et al. | |
| 8,062,308 B2 | 11/2011 | Noda et al. | |
| 8,647,352 B2 | 2/2014 | Noda et al. | |
| 2005/0192629 A1 | 9/2005 | Saadat et al. | |
| 2007/0225762 A1 | 9/2007 | LaBombard | |
| 2009/0105728 A1 | 4/2009 | Noda et al. | |
| 2009/0157101 A1 | 6/2009 | Reyes et al. | |

OTHER PUBLICATIONS

Wayne A. Noda, "Devices and Methods for Securing Tissue", file history of related U.S. Appl. No. 14/714,730, filed May 18, 2015.

Wayne A. Noda, Stephen Graham Bell, "Devices and Methods for Securing Tissue", file history of related U.S. Appl. No. 14/043,038, filed Oct. 1, 2013.

"6 Shooter Universal Saeed Mufti-Band Ligator", Cook Medical, Retrieved on Aug. 1, 2015 from https://www.cookmedical.com/products/esc_mbl_webds/.

* cited by examiner

DELIVERY ASSEMBLY FOR RESILIENT TISSUE CLAMP

This application claims is a continuation in part of U.S. patent application Ser. No. 13/477,649, filed May 22, 2012, which claims priority from U.S. provisional patent application 61/492,289, filed Jun. 1, 2011. Priority is claimed from both of these documents and both are incorporated herein by reference.

This application is also a continuation in part of U.S. patent application Ser. No. 13/240,018, filed Sep. 22, 2011, which is a continuation of U.S. patent application Ser. No. 12/141,391, filed Jun. 18, 2008, now U.S. Pat. No. 8,062,308, which in turn claims priority from U.S. provisional patent application Ser. Nos. 60/982,083, filed Oct. 23, 2007 and 61/012,124, filed Dec. 7, 2007. Priority is claimed to all of the above documents and all are incorporated herein by reference.

FIELD OF THE INVENTION

The present application relates generally to devices and methods for securing tissue.

BACKGROUND OF THE INVENTION

Internal body tissue sometimes must be secured together for various reasons. As an example, diverticulosis is an unfortunately common condition in which an area of the intestine bulges out into the peritoneal cavity to form a sac referred to as a "diverticulum". The above-referenced patent envisions a natural orifice method for resolving diverticulum by inverting them and then securing opposed serosal surfaces together using a ring to thereby tightly and securely close off the affected tissue to alleviate the risk of peritonitis.

SUMMARY OF TILE INVENTION

As understood herein, it would be advantageous to provide a delivery assembly to facilitate accurate and easy delivery of the ring onto the target tissue and that could employ an off the shelf endoscope to do so without requiring manufacturer modification of the endoscope.

Accordingly, a delivery assembly for a tissue compression ring includes a ring sleeve that fits snugly over a main endoscope over a distal end of the endoscope. An extension tube projects distally away from the ring sleeve. The extension tube defines a first axis, the ring sleeve defines a second axis, and the first and second axes are parallel to each other and are not collinear with each other. In one example, the ring sleeve is open ended in the area above the extension tube so that the optics, light source and lens washer are unobstructed. An inner carrier is reciprocatingly disposed inside the extension tube and is configured for carrying one or more resilient tissue compression rings in a stretched configuration on the inner carrier. The inner carrier is configured for attachment to an actuator that can be pulled proximally to move the inner carrier proximally within the extension tube, pulling a compression ring on the inner carrier into contact with a distal end of the extension tube. Continued pulling of the inner carrier causes the compression ring to be pushed off the inner carrier onto target tissue, at which point the compression ring is relaxed to assume a small configuration and clamp target tissue.

In example embodiments the extension tube is made integrally with the ring sleeve and the inner carrier can be tube-like. The extension tube is made to hermetically seal against the distal end of the endoscope at the orifice of the working channel so that vacuum from the working channel can be communicated to the distal end of the extension tube. Vacuum serves to invert the diverticulum prior to deployment of the tissue compression ring. The inner diameter of the extension tube may be marginally larger than the outer diameter of the inner carrier such that the inner carrier is supported by the extension tube as the inner carrier moves within the extension tube.

In some examples the actuator is cable that extends through a working channel of the endoscope into the extension tube. The ring sleeve may define a distal end and the extension tube may define a proximal periphery at least partially abutting the distal end of the ring sleeve. If desired, a tongue can extend proximally from the extension tube along the ring sleeve in contact with the ring sleeve for structural strengthening.

In another aspect, an assembly for adapting an endoscope for delivery of a tissue compression ring includes an extension body fittable onto a distal end segment of the endoscope by hand with an actuator cable extending through the endoscope into the extension body. A carrier element is connectable to the actuator and bears at least one tissue compression ring. The actuator is movable by a person to move the carrier element relative to an abutment element defined by the extension body to move the tissue compression ring against the abutment element and off the carrier element onto target tissue.

In another aspect, a method includes instructing a person to fit an extension body onto a distal end segment of an endoscope with an actuator cable extending through the endoscope into the extension body. The method also includes instructing a person to place at least one tissue compression ring onto a carrier element movably engaged with the extension body, and to activate an actuator to move the carrier element such that the compression ring is urged off the carrier element onto target tissue visualizable through the endoscope.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
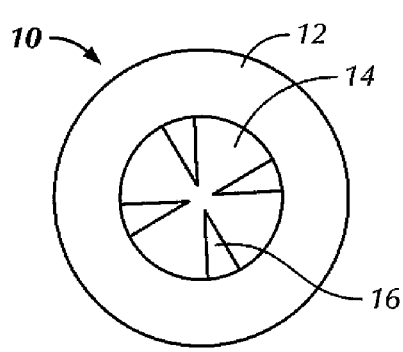
FIG. 1 is a plan view of an example compression ring according to present principles.
Figure 2:
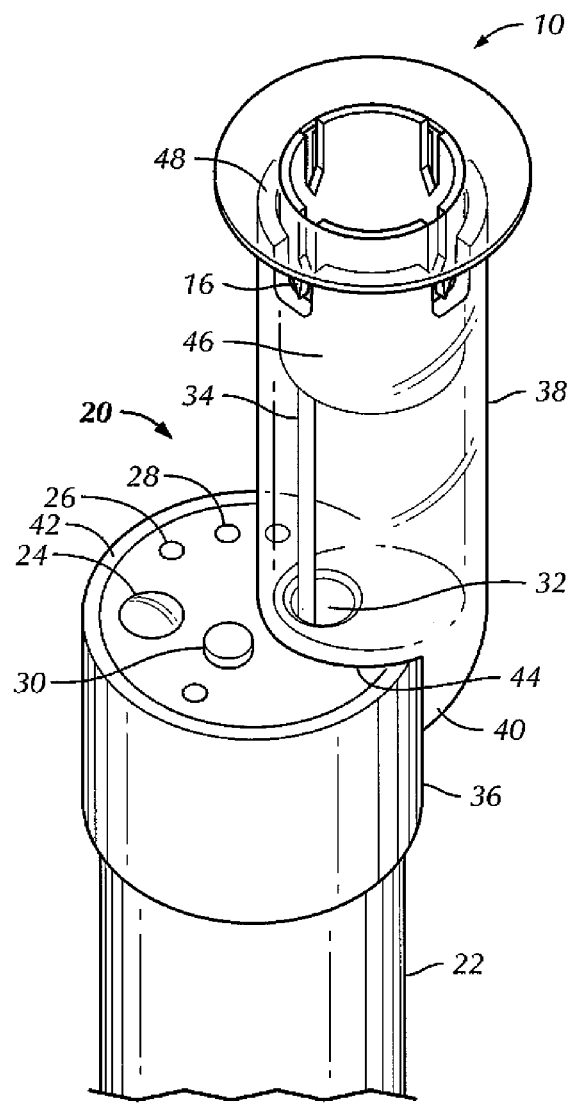
FIG. 2 is a perspective view of the delivery assembly showing the ring on the assembly with spikes oriented proximally and showing portions of the assembly transparently to reveal interior structure, with the inner carrier in the retracted position to deploy the tissue compression ring.
Figure 3:
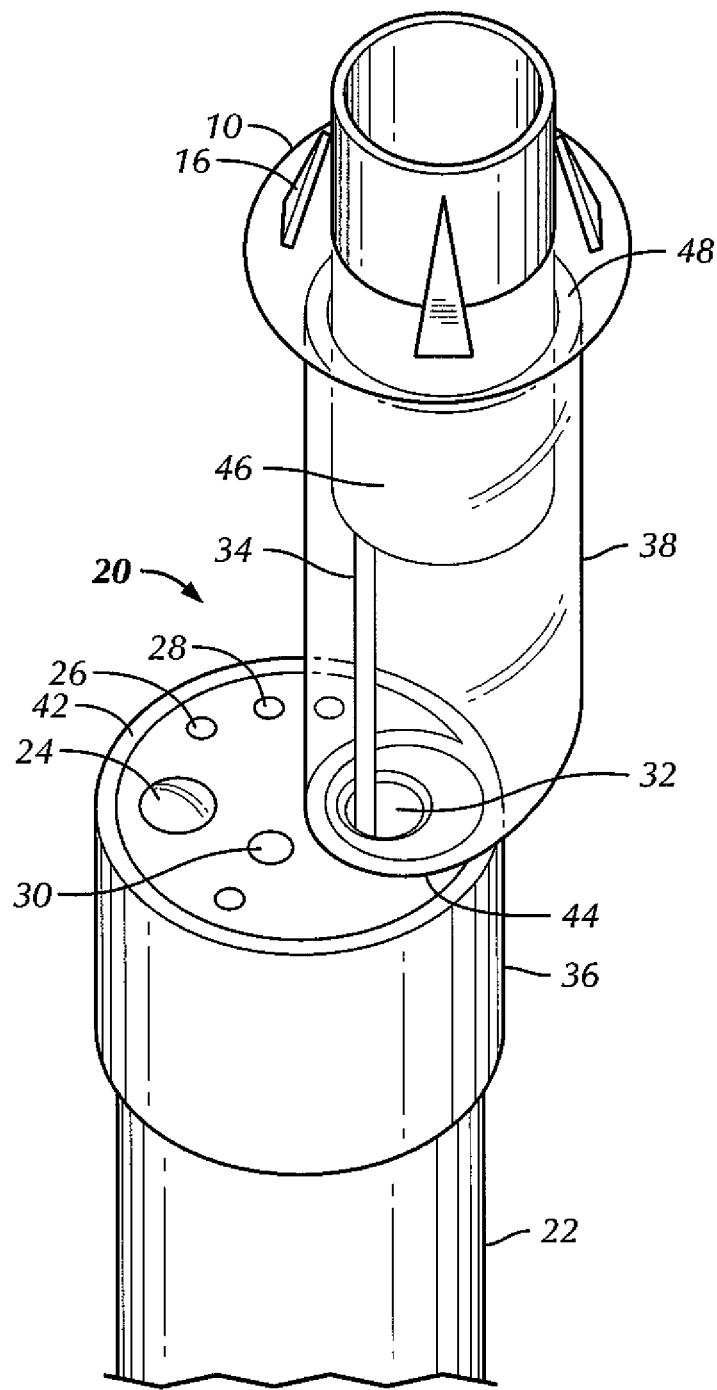
FIG. 3 is a perspective view of the delivery assembly showing the ring on the assembly with spikes oriented distally and showing portions of the assembly transparently to reveal interior structure, with the inner carrier in the extended position to hold the tissue compression ring and omitting the tongue for ease of disclosure.

Referring initially to FIG. 1, an example non-limiting compression ring 10 is shown that may be used in connection with the delivery assembly shown in FIGS. 2 and 3. It is to be understood that other compression rings may be used, e.g., any suitable rings shown and described in the above-referenced patent, and that the ring in FIG. 1 is exemplary only.

As shown, the ring 10 includes a toroidal resilient hollow body 12 defining a compression channel 14. Four tissue spikes 16 are embedded in the body 12 and are equidistantly radially spaced from each other, extending into the compression channel 14 with the ends of the spikes 16 meeting substantially in the center (axis) of the channel.

In a relaxed state, the ring 10 assumes a radially smaller configuration, and is resilient so that it can be stretched to a radially enlarged state to fit onto the carrier described below. The body 12 can be plastic or rubber and may contain a drug eluting material. The body 12 may be coated with and then elute drugs such as antiinflammatories, antibiotics, antibacterial drugs, and tissue healing factors. The drug coating can include a bioabsorbable polymer that is loaded with the drug that releases over time.

In one implementation, for example, the body 10 and/or gripping elements such as spikes may be coated with a polymer such as Polyglycolic-Lactic Acid (PGLA) layers. The layers may be, e.g., bonded to the spikes. The PGLA can be loaded with a carrier drug that elutes as the PGLA absorbs. PGLA can be solubilized in a vapor form by dissolving it in a solvent such as, e.g., dimethyl formamide (DMF). This composition can then have the required drug added, and then sprayed in layer coatings onto the spike or the body. The dosage can be by weight. Furthermore, antimicrobials, anti-inflammatories, heavy weight proteins such as tissue growth factors, etc. may also be mixed into the composition to help with wound healing. The drug eluting coating can be applied with no primer and then heat set onto the spikes or ring.

With this in mind, it may be appreciated that when the compression ring is pushed off the delivery device onto, e.g., a diverticulum, the ring collapses around the diverticulum as the ring assumes the relaxed configuration, with the diverticulum captured and compressed in the compression channel 14. Furthermore, owing to its material bias the ring 10 twists about its circumference into the relaxed configuration, wherein the spikes/gripping elements 16 extend perpendicularly to the compression channel 14, penetrating the tissue owing to the hoop strength of the compression ring.

FIGS. 2 and 3 show a delivery assembly 20 for delivering the tissue compression ring 10. In FIG. 2 the ring 10 is stretched onto the assembly 20 with the engagement members (spikes) 16 oriented proximally, whereas in n FIG. 3 the ring 10 is stretched onto the assembly 20 with the engagement members (spikes) 16 oriented distally.

As shown, the assembly 20 is engaged with an endoscope 22. The endoscope 22 may contain several channels. In the example shown, the endoscope 22 includes a camera lens 24 which, via fiber optics, sends images back through a fiber lumen in the endoscope 22 to a display assembly external to a patient for viewing of images within the patient by a medical caregiver. The example non-limiting endoscope 22 also may include one or more illumination sources 26 such as light emitting diodes (LED), which receive power through a lead extending through a lead lumen in the endoscope Fiberoptic light sources may also be used. Also, the endoscope 22 may include an irrigation lumen 28 through which irrigating fluid such as water or saline may be directed onto tissue. A lens cleaner 30 may also be provided.

In addition, a working channel 32 may be formed in the endoscope 22, and an actuator such as a cable or wire or string 34 positioned in the working channel 32 to extend out of the proximal end of the endoscope so that it can be manipulated by a person for purposes to be shortly disclosed. The working channel can be connected to a source of vacuum to draw tissue into the below-described delivery assembly without impeding the filed of view of the lens 24.

Having described the endoscope 22, attention is now turned to the delivery assembly 20. A ring sleeve 36 fits snugly over the distal end segment of the endoscope 22 as shown. The ring sleeve is hollow and cylindrical and may substantially completely surround the endoscope in a tight friction or press fit, so that a person can engage the ring sleeve 36 with the distal segment of the endoscope by hand by simply sliding the ring sleeve onto and past the distal end of the endoscope. Owing to the snug fit between the inner surface of the ring sleeve 36 and the outer surface of the endoscope 22, the ring sleeve remains in the position shown in FIGS. 2 and 3 until such time as a person employs sufficient force to pull the sleeve off the endoscope. However, in some embodiments the ring sleeve may be bonded or otherwise more tightly affixed to the endoscope to prevent a person from pulling the ring sleeve off the endoscope.

As shown in FIGS. 2 and 3, an extension tube 38 projects distally away from the ring sleeve 36 and, hence, projects distally away from the distal end of the endoscope 22 as shown. The extension tube 38 is hollow and can be cylindrical in shape or it may have an oblong or ovular or other cross-section. In any case, in the example shown the axis of the extension tube 38 can be parallel to but spaced from (not collinear with) the axis of the ring sleeve 36. In some embodiments the ring sleeve 36 and extension tube 38 are made integrally together by, e.g., injection molding them as a single piece. In other implementations the sleeve 36 is made separately from the tube 38 and the two are joined by, e.g., solvent bonding. If desired, an elongated tongue 40 (FIG. 2) of the end tube 38 may extend back and along the ring sleeve 36 for added structural strength. Note that in the embodiment shown, the ring sleeve 36 defines an open distal end 42 and the extension tube 38 defines a proximal periphery 44 which at least partially abuts the distal end 42 of the ring sleeve 36 and which can be hermetically sealed to the working channel of the endoscope. In this way tissue can be vacuumed into the extension tube without impeding the field of view or illumination at the distal end of the endoscope. As an alternative to an open ended ring sleeve for clearance of optics, the portion of the distal end of the ring sleeve not covered by the extension tube can be covered with an optically clear glass or plastic.

As shown in FIGS. 2 and 3, an inner carrier 46, which may be a tube or tube-like, is disposed inside the extension tube 38. The carrier 46 is configured for carrying one or more resilient tissue compression rings 10 as shown in a stretched configuration on the inner carrier 46.

As shown, the inner carrier 46 is attached to the actuator 34 and as shown in cross-reference to FIGS. 2 and 3, the inner carrier 46 can reciprocate within the outer tube 38 between an extended position (FIG. 3), in which the compression ring 10 is engaged with the carrier 46 without any axial force acting on the ring 10 to move it off the carrier 46, and a retracted position (FIG. 2), in which the actuator 34 has been pulled proximally to pull the carrier 46 proximally until the compression ring 10 is pulled against the distal periphery 48 of the extension tube 38. At this point, continued proximal pulling of the inner carrier 46 causes the compression ring 10 to be pushed off the inner carrier 46 by the distal end 48 of the extension tube 38 onto target tissue, at which point the compression ring 10 relaxes, through material bias, to assume a small configuration and clamp target tissue.

It can be appreciated in reference to FIGS. 2 and 3 that the inner diameter of the extension tube 38 preferably is marginally larger than the outer diameter of the inner carrier 46. By "marginally larger" is meant that there is not tight interference fit between the extension tube 38 and inner carrier 46 that would unduly impede a person from pulling the inner carrier 46 within the outer tube 38. Indeed there may be a slight radial space between the inner carrier and outer tube. In any case it is preferred that the inner diameter of the extension tube 38 is marginally larger than the outer diameter of the inner carrier 46 so that the extension tube 38 can provide a radial bearing surface for the inner carrier 46 as it moves within the outer tube.

With the above structure in mind, a person can be instructed to fit the ring sleeve 36 onto the distal end segment of the endoscope 22 with the actuator cable 34 extending through the endoscope 22 into the extension tube 38. Essentially the actuator 34, which is attached to the carrier 46, is first inserted into the working channel 32 of the endoscope 22 from the distal end of the endoscope 22 and then the ring sleeve 36 is fitted onto the endoscope. A person is then instructed to place at least one tissue compression ring 10 onto the inner carrier 46 while the inner carrier is in the extended position shown in FIG. 3. The person is instructed to activate an actuator to move the carrier proximally such that the compression ring 10 is urged off the carrier 46 onto target tissue that can be visualized through the endoscope 22. Note that all steps are reversible and repeatable so that this ring deployment can be accomplished multiple times on a single patient to treat multiple diverticulum.

While the particular DELIVERY ASSEMBLY FOR RESILIENT TISSUE CLAMP is herein shown and described in detail, it is to be understood that the subject matter which is encompassed by the present invention is limited only by the claims.

What is claimed is:

1. A delivery assembly for a tissue compression ring, comprising:
    a ring sleeve that fits snugly over a main endoscope over a distal end of the endoscope;
    an extension tube projecting distally away from the ring sleeve, the extension tube defining a first axis, the ring sleeve defining a second axis, the first and second axes being parallel to each other and not being collinear with each other;
    an inner carrier reciprocatingly disposed inside the extension tube and configured for carrying one or more resilient tissue compression rings in a stretched configuration on the inner carrier, wherein the inner carrier is configured for attachment to an actuator that can be pulled proximally to move the inner carrier proximally within the extension tube, pulling a compression ring on the inner carrier into contact with a distal end of the extension tube, wherein continued pulling of the inner carrier causes the compression ring to be pushed off the inner carrier onto target tissue, at which point the compression ring is relaxed to assume a small configuration and clamp target tissue.

2. The assembly of claim 1, wherein the extension tube is made integrally with the ring sleeve.

3. The assembly of claim 1, wherein the inner carrier is tube-like.

4. The assembly of claim 3, wherein an inner diameter of the extension tube is marginally larger than an outer diameter of the inner carrier.

5. The assembly of claim 1, wherein the actuator is cable, wire, or string.

6. The assembly of claim 5, wherein the cable extends through a working channel of the endoscope into the extension tube.

7. The assembly of claim 1, wherein the ring sleeve defines a distal end and the extension tube defines a proximal periphery at least partially abutting the distal end of the ring sleeve.

8. The assembly of claim 7, further comprising a tongue extending proximally from the extension tube along the ring sleeve in contact with the ring sleeve.

9. The assembly of claim 1, wherein the ring sleeve has an open distal end or a distal end covered by optically transmissive plastic or a combination thereof.

10. The assembly of claim 1, wherein the extension tube is sealed to a working channel of the endoscope through which a vacuum is establish in the extension tube.

11. Assembly for adapting an endoscope for delivery of a tissue compression ring defining a central ring axis passing perpendicularly through an opening of the tissue compression ring, the assembly comprising:
    an extension body fittable onto a distal end segment of the endoscope by hand with an actuator extending through the endoscope into the extension body, the extension body defining an extension body axis extending perpendicularly through an opening defined by the extension body;
    a movable element connectable to the actuator, the movable element defining a movable element axis extending perpendicularly through an opening defined by the movable element, at least one of: the movable element; extension body bearing at least one tissue compression ring; wherein
    the actuator is movable by a person to move the movable element to thereby move an abutment element against the tissue compression ring onto target tissue, wherein when the extension body is on the distal end segment of the endoscope, the extension body axis, movable element axis, and central ring axis are all parallel to a longitudinal axis defined by the endoscope, the extension body axis not being co-linear with the longitudinal axis defined by the endoscope.

12. The assembly of claim 11, wherein the extension body includes:
    a ring sleeve that fits snugly onto the distal end segment of the endoscope; and
    an extension tube projecting distally away from the ring sleeve.

13. The assembly of claim 12, wherein the extension tube defines a first axis, the ring sleeve defines a second axis, and the first and second axes are parallel to each other and are not collinear with each other.

14. The assembly of claim 12, wherein the movable element is established at least in part by an inner carrier reciprocatingly disposed inside the extension tube and configured for carrying one or more resilient tissue compression rings in a stretched configuration.

15. The assembly of claim 12, wherein the abutment element is established at least in part by a distal end of the extension tube.

16. The assembly of claim 12, wherein the extension tube is made integrally with the ring sleeve.

17. The assembly of claim 14, wherein the inner carrier is tube-like.

18. The assembly of claim 17, wherein an inner diameter of the extension tube is marginally larger than an outer diameter of the inner carrier.

19. The assembly of claim 12, wherein the ring sleeve defines a distal end and the extension tube defines a proximal periphery at least partially abutting the distal end of the ring sleeve.

20. The assembly of claim 19, further comprising a tongue extending proximally from the extension tube along the ring sleeve in contact with the ring sleeve.

\* \* \* \* \*